United States Patent [19]

Alihanka et al.

[11] 4,320,766
[45] Mar. 23, 1982

[54] APPARATUS IN MEDICINE FOR THE MONITORING AND OR RECORDING OF THE BODY MOVEMENTS OF A PERSON ON A BED, FOR INSTANCE OF A PATIENT

[75] Inventors: Jukka Alihanka, Littoinen; Kaarle Vaahtoranta; Stig-Eyrik Björkqvist, both of Turku, all of Finland

[73] Assignee: Instrumentarium Oy, Helsinki, Finland

[21] Appl. No.: 128,835

[22] Filed: Mar. 10, 1980

[30] Foreign Application Priority Data

Mar. 13, 1979 [FI] Finland ................................. 790847
Nov. 27, 1979 [FI] Finland ................................. 793713

[51] Int. Cl.³ .............................................. A61B 5/10
[52] U.S. Cl. .................................... 128/671; 128/714; 128/722; 128/782; 340/562
[58] Field of Search ............... 128/722, 748, 714, 715, 128/721, 782, 670–671; 361/283, 330; 324/454, 457; 73/780, 724, 718; 310/310; 340/562; 179/111 ET

[56] References Cited

U.S. PATENT DOCUMENTS

| | | | |
|---|---|---|---|
| 3,572,316 | 3/1971 | Vogelman et al. | 128/671 |
| 3,821,491 | 6/1974 | Whetstone et al. | 179/111 E |
| 3,875,481 | 4/1975 | Miller et al. | 361/283 |
| 3,926,177 | 12/1975 | Handway et al. | 128/722 |
| 3,991,746 | 11/1976 | Hanna | 128/722 |
| 3,996,922 | 12/1976 | Basham | 128/722 |
| 4,152,748 | 5/1979 | Arkans | 361/283 |

Primary Examiner—Robert W. Michell
Assistant Examiner—John C. Hanley
Attorney, Agent, or Firm—Keil & Witherspoon

[57] ABSTRACT

A capacitive motion sensor placed under a mattress or the like for monitoring the movements of a person. The sensor uses an active layer consisting of two courses of dielectric material placed in contact with one another. Movements of a person on top of the mattress cause the courses to move relative to one another, thereby generating an electric change in the active layer which is detected by a pair of spaced elements which form a capacitive antenna means.

11 Claims, 7 Drawing Figures

APPARATUS IN MEDICINE FOR THE MONITORING AND OR RECORDING OF THE BODY MOVEMENTS OF A PERSON ON A BED, FOR INSTANCE OF A PATIENT

FIELD OF INVENTION

The present invention concerns an apparatus in medicine for monitoring and/or recording the body movements of a person on a bed, for instance of a patient, to the purpose of monitoring e.g. epileptic convulsive seizures, other deviant moving, tremor, respiration, mechanical cardiac function or any other equivalent motorics of the patient or subject under examination or the changes therein.

BACKGROUND OF INVENTION

Regarding the state of art relevant to the invention, reference shall be made to the Finnish Pat. No. 55113 wherein bioelectrical functions are observed by measurement of the reactance between an electrode attached to the patient and an electrically conductive antenna outside the patient. The object of the present invention is to develop further the invention disclosed in said reference so that its range of application may be enlarged and the use of electrodes affixed to the patient may be avoided.

It is known in prior art to record the body movements caused by the heartbeat, the so-called cardiac recoil movements, by means of ballistography. In such recording, the patient is supine on a bed which has been tuned to be supported by various kinds of spring systems, wherein the cardiac recoil movement in various planes may be observed and monitored. The method is expensive and requires a well-balanced apparatus and a vibration-free room. Therefore the application of this method in clinical use has remained insignificant. In prior art are known various patient pulse monitoring systems for instance, in which special electrodes have to be connected to the patient and such electrodes, when they become detached, produce as a rule a false alarm. Moreover, during waking time the wearing of these electrodes induces psychological stress. On the other hand the harmful false alarms have on the staff's side been experienced as unsatisfactory, even to such degree that it is preferred to leave the automatic alarms switched off because the false alarms disturb the nursing staff as well as the patients in the ward. Furthermore, the electrodes affixed to the patient restrict the patient's mobility.

SUMMARY OF INVENTION

In order to eliminate the drawbacks mentioned, an apparatus is proposed in the invention wherein the said person has been placed in a bed of a kind fitted with antenna means which communicate with amplifier and recording means and potentially also with alarm means, and said antenna means registering the quantitative and/or local changes in the static charges produced by the movements of the person lying on said bed in his clothing, in the bedclothes and/or in the mattress, the potential differences generated by said changes of charge in the antenna means being amplified and the electric signal thus obtained being monitored and/or employed as a supervision signal.

A favourable embodiment of the invention is characterized in that it comprises, disposed under the mattress of the bed, an antenna means comprising two antenna plates, nets, rods or equivalent spaced from each other. In particular, the antenna means may consist of metal foils mounted on the opposite surfaces of an insulating course, whereby it is possible to make the whole antenna means thin and flexible.

A particularly advantageous embodiment is obtained by connecting to the antenna means an active course, of which the electrostatic state of charge varies as a consequence of the movements acting on it, the antenna means and the active course having been placed upon each other to constitute an extra mattress for placement under the patient or under the mattress.

The monitoring system employed in association with a bed fitted with the apparatus of the invention is mainly characterized in that the system comprises one or several beds of the kind described and that the system comprises, for each bed, a specific pre-amplifier and a shielded lead by which the antenna of each bed is connected to the pre-amplifier, and that the system further comprises signal processing means, recording and/or monitoring means and, if required, alarm means either in the patient room or in a particular control room. In accordance with the teachings of the invention a new apparatus is obtained, which shall be referred to, in the following, by the abbreviation "SCSB apparatus" (Static Charge Sensitive Bed). Among the most important applications of the invention are: recording of the motorics during sleep, observation of the patient in the waking state also, to the purpose for instance of noticing epileptic seizures, or any other deviant motion. In addition is it possible to measure the patient's tremor, its amplitude and the changes therein at various times or, for instance, under drug effect. The apparatus of the invention is also particularly well suited for monitoring the vital functions of neonates.

The respiratory movement produces in the SCSB recording according to the invention, a slow undulation in step with the breathing, to elicit (render observable) with the SCSB signal has to be filtered so that the slow signal components in the range of about 0.2 to 3 Hz are accentuated. This may be done in that the higher frequences are filtered out with an adjustable band pass filter, whereupon the respiratory variation will show up when the gain is increased. The patient's respiration may be followed with ease even over prolonged periods by using recorder monitoring with slow chart speed. Such recording possesses significance diagnostically as well, for instance in the observing of sleep apnoea, of the so-called Cheyne-Stokes respiration type, which are associated with certain diseases.

The SCSB recording according to the invention may also be applied in examination of the cardiac mechanics. In SCSB recording, the cardiac recoil movement produces a deflection resembling greatly the ballistographic curves recorded by earlier methods. The SCSB ballistograph is not fully equivalent to any known component signal of the ballistograph: it is rather a kind of sum-total graph of the same phenomenon. However, the information which it provides with a view to clinical significance affords a wealth of information, and in all likelihood enough information to enable inferences to be drawn from changes occurring in the cardiac mechanics. Owing to the ease of use of the apparatus, SCSB ballistography is believed to have clinical significance, and the information afforded by ballistography could be utilized more efficiently clinically in the future. It is also an advantage that the patient need not be transported from one place to another for the duration of the recording and that it would be possible to make prolonged, and even continuous, recordings.

It is also possible, utilizing the SCSB ballistography taught by the present invention, to observe the patient's pulse by filtering with an adjustable band pass filter the signal in such manner that the ballistography waves are set out from the background noise, whereby it is possible to use methods known in the art for observing the pulse with the aid of various display instruments and monitors. Moreover, the invention may be incorporated in an automatic alarm system which may be used towards patient supervision and observing. It is possible to observe the pulse, respiration, movements, for instance during the night, without disturbing the patient.

Since the applying of the invention requires no separate electrodes to be connected to the patient, this reduces the extra phychological stress associated with the control situation, which has been considered a detrimental factor in the systems of prior art. In the SCSB systems, alarm will be actuated when the ballistographic cardiac movement ceases or when the breathing stops. The system of the invention does not restrict the patient's mobility. When the patient rises from his bed, he switches the system off, or this may also be automatically effected in that when the patient's weight is taken off the bed, a weight switch makes the system inoperative.

In the following, the invention shall be described in greater detail with reference being made to certain embodiment examples of the invention and to various records produced with the aid of an apparatus according to the invention, presented in the figures of the attached drawings.

BRIEF DESCRIPTION OF THE DRAWINGS

FIG. 1A shows a partial section of FIG. 1, carried along the Line A—A, on an enlarged scale, and FIG. 1B illustrates the capacitive coupling of the apparatus.

DETAILED DESCRIPTION OF THE INVENTION

Figure 1:
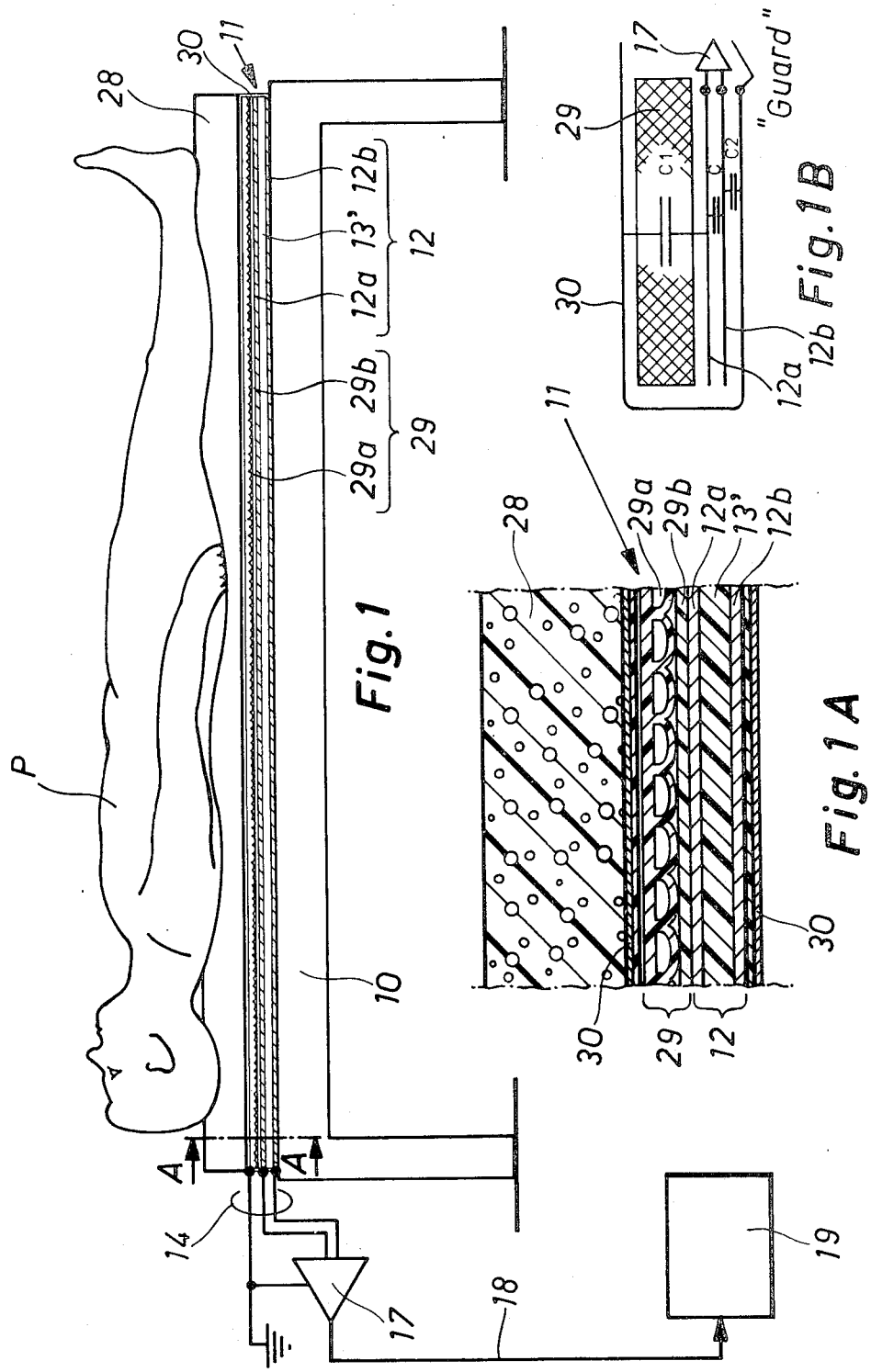
FIG. 1 presents, schematically, an apparatus according to the invention, in elevational view.

Referring now to FIG. 1, therein is shown the patient, or the person under examination, P, recumbent on the bed 10 comprising a recording mattress 11 and thereupon, most properly a foamed plastic mattress 28. The patient has normal bedclothes and clothing. The recording mattress 11 comprises two metal plates 12a and 12b of the same size and shape, or equivalent metal nets, rods or gratings, and which serve as antennas. Between the metal plates 12a and 12b lies an insulating plate 13, which serves as insulation between the antenna plates 12a and 12b as well as their mechanical support so that the antenna plates 12a and 12b can be made in the form of comparatively thin films affixed on the surface of the insulating board 13.

The metal plates 12a and 12b have been connected by a shielded lead 14 to a pre-amplifier 17, which is for instance a conventional differential amplifier of the kind used in ECG techniques, characterized by a high input impedance. As shown in FIG. 1, the differential amplifier 17 has been connected by a shielded cable to the monitoring and recording means 19.

Even the smallest movement of the patient P lying on the bed 10, for instance the adduction of one finger, will cause in the clothing of the patient P, or of the person under monitoring or examination, in the bedclothes and/or in the active layer 29 of the mattress, quantitative and local changes of static charges, which generate potential differences between the antenna plates 12a and 12b, which plates have been placed as close as possible to the patient or to the active layer 29 in view of accomplishing the closest possible coupling between the antenna means 12 and the sources which produce the said change of charges.

In the embodiment presented, the active layer 29 consists of two juxtaposed, insulating materials 29a and 29b with different dielectric constants. Suitable materials are for instance plastics having mutually different dielectric constants. It is also a characteristic feature of the construction of the active layer 29: that its courses are able to move with reference to each other, however maintaining their contact. The movement takes place so that the points of contact between the materials change. To this purpose, in the embodiment presented, the layer 29a consists of blister plastic, its air-filled blisters constituting "anti-friction elements" by virtue of which the courses 29a and 29b can move lightly with reference to each other.

Under the active layer 29 are located the above-described antenna means 12 for measurement of the charge distribution in the active layer.

Furthermore, the active layer 29 and the antenna means 12 have been inserted in a shield 30 consisting of conductive, flexible material and which is connected to the ground of the measuring amplifier 17. In practice, the shield 30 may be made of a bag of plastic film metallized on the outside. Since the antenna equipment 12 as well may be made of plastic film 13 of which the opposite faces have been provided with metallic films 12a and 12b, the recording mattress can be made thin and foldable.

The mode of operation of the recording mattress above described is as follows. The body movements of the patient P are transmitted through the foamed plastic mattress 28 to the active layer 29, where the materials 29a and 29b of different dielectric, insulating substances are set in motion with reference to each other so that their points of contact vary by effect of the movement. It is well known that this results in the generation of electrical superficial charges of different signs on said material courses 29a and 29b. These superficial charges constitute electrical dipoles, of which the electric fields are transmitted to the antenna means 12, the signal therefrom obtained being recorded with the aid of the amplifier 17. The recorded signal conforms to the patient's movements because the orientation and number of dipoles, and consequently also their fields, vary under effect of the movement. On the other hand, the metallic surfaces of the shield 30 and the antenna plates 12a and 12b form between themselves capacitors, and since the active layer 29 consists of a resilient material, the capacitance of the metal plates on either side thereof will vary, and this causes changes of voltage in the statically charged capacitors.

Based hereon, the recording mattress of the invention may also be constructed as follows (FIG. 1B).

The antenna means 12a,12b have been so disposed that upon them is an active layer 29, and these have been placed in a continuous shield 30 which is internally electrically insulating but has been coated with a conductive substance. The active layer 29 is an insulating layer fitting the purpose. The structure will then operate as follows.

The antenna means consist, as has been described above, of two mutually insulated, conductive material courses 12a and 12b, which together form a capacitance C. The conductive shield 30 then forms a capacitance C2 with the course 12b and the capacitance C1 with the course 12a. The capacitances C2 and C1 differ in magnitude and, moreover, due to the construction so that C2 is far greater than C1. Upon this structure the foamed plastic mattress 28 is placed, on which the experimental subject P lies down. The subject's movements are transmitted through the foamed plastic 28 into the arrangement thereinunder so that, first of all, C1 changes because the layer 29 consists of a highly resilient material. With an active layer 29 as shown in FIG. 1A, the distance of the charged courses from the antenna means 12 and from the bag 30 serving as shield will also change. In addition, the movement gives rise to static charges in the active layer, and to local changes in them.

In the case of FIG. 1B, the capacitance C1 may also be charged by means of an external voltage source, or one may for the insulator 29 use a substance on which the charges have been permanently imposed.

By effect of the factors enumerated above, the voltage across the capacitor C1 changes in the first place, and these changes are transmitted to the antenna means and to the capacitor C constituted by them.

By the aid of the construction described, the following advantages are gained, among others.

The plates 12a and 12b acting as antenna means and which become coupled to the input terminals of the amplifier are symmetrical with reference to external interference fields but they are asymmetric regarding the changes of charge taking place in the active layer 29. The bag 30 serving as shield transmits the changes of the charge field induced by the movements, to the antenna plates, acting at the same time as an efficient shielding against external interference fields. This protective bag 30 is connected to the ground terminal, or to a potential "Guard" terminal, of the measuring amplifier 17.

Figure 2:
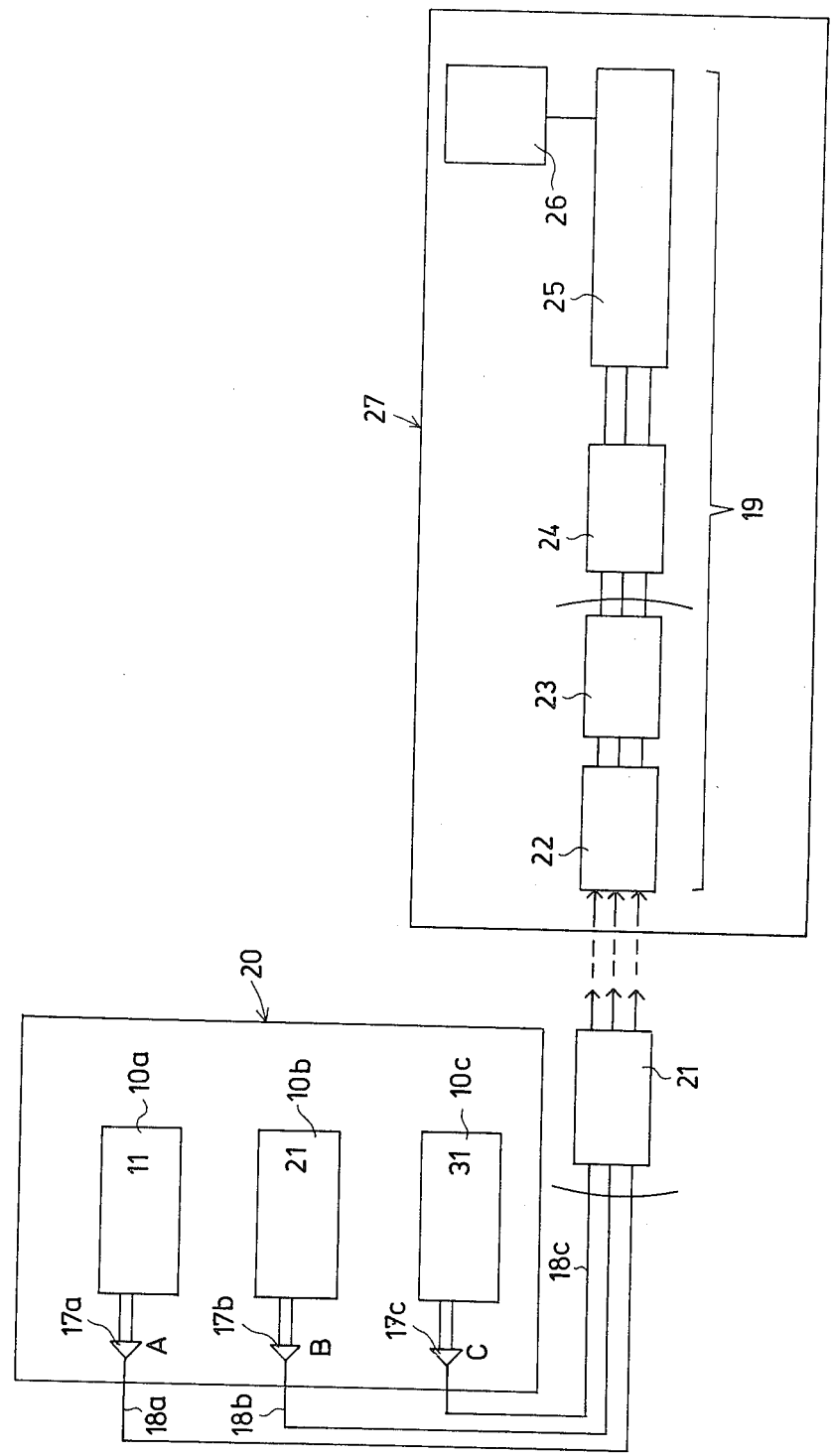
FIG. 2 presents, in the form of a block diagram, one embodiment of the monitoring and control system for applying the apparatus of the invention.

In FIG. 2 is shown a hospital monitoring and control system applying the means of the invention. This system comprises the patient room 20, where beds 10a, 10b, 10c etc. provided with antennas of the kind described have been placed, their antennas being connected by cable to the pre-amplifiers 17a, 17b, 17c etc., and these in turn by shielded cables 18a, 18b, 18c to the monitoring and recording equipment 19. Since it is frequently unavoidable that the patient room 20 is quite far away from the control room 27, a special electric transmission system must be used between these rooms, wherein modulation is employed and, for instance, the time sharing principle. Such systems are known in the art in themselves and their closer description shall therefore be omitted. FIG. 2 displays, of components belonging to this system: a line driver 21, multiplex 22, and line receiver 23.

The signals derived from the receiver 23 are conducted to a signal processing means 24 with among other things, a 50 Hertz tank circuit and adjustable band pass, which is selected suitably for each particular application; for instance, in respiration monitoring the band is in the range from 0.2 to 3 Hz, for the movement pick-up in the night-time it is 0.5 to 100 Hz. The signal processing circuit may perform, for instance, a frequency analysis of the incoming signal. After the signal processing circuit 24, the signals are carried to the monitor or recorder 25, both of which are devices known in themselves in the art. One may use, for monitor 25: an oscilloscope, conventional recorders, e.g. an ECG recorder. With the monitor 25 has been connected an alarm device 26, which actuates an alarm for instance in case the patient's respiration or heart movements stop completely, or if these movements display a remarkable deviation from normal. The alarm device 26 is preferably arranged to be triggered by the signal amplitude e.g. when the respiration amplitude falls below a given limit or the ballistographic undulation falls below a given limit or drops out. Triggering of the alarm device is, for instance, on the basis of the pulse display triggered by the ballistographic undulation when this pulse falls below a predetermined limit.

Figure 3:
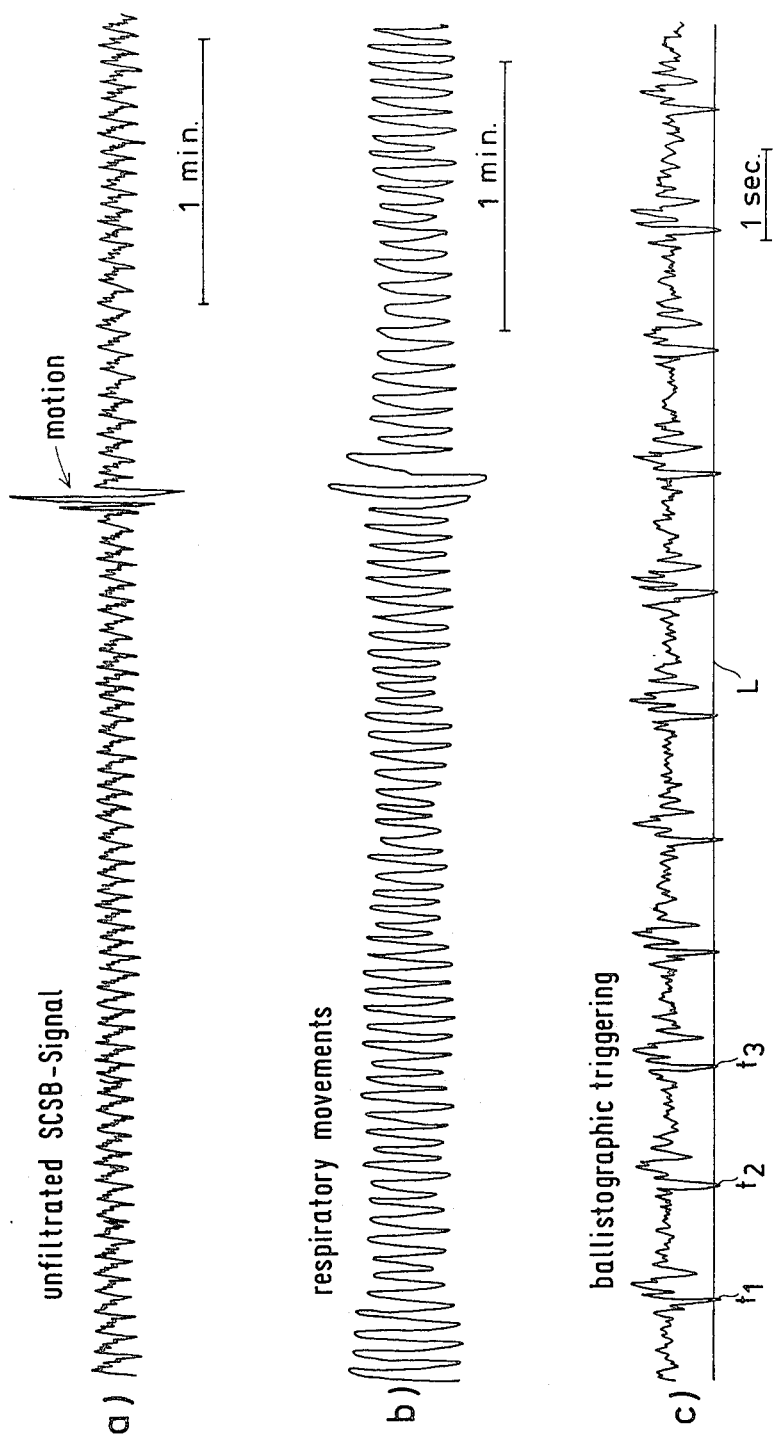
FIG. 3 displays three different records, whereof record a shows the unfiltered SCSB signal recorded with an apparatus according to the invention, record b represents the respiratory movements, and the record c illustrates a recording in connection of which ballistographic triggering is employed.

FIG. 3 displays three different signals recorded by the method of the invention. The recording a is the unfiltered SCSB signal according to the invention, and the figure b presents the same signal after its conduction through a low pass or band pass filter, for instance a filter having its band in the range from 0.2 to 3 Hz. Hereby the undulation caused by the respiratory movements will show up with emphasis in the record. The record reproduced in FIG. 3c illustrates the principle of ballistographic triggering. In connection with the recording function, a given voltage level L has been set, by default of which the triggering events t1, t2, t3 etc. are obtained. The number of such triggerings per unit time is a measure e.g. for the heart rate, and when this quantity falls below a pre-set limit, triggering of the alarm device 26 ensues.

The record c in FIG. 3 illustrates the above-described principle of ballistographic triggering in its application in the method of the invention.

Figure 4:
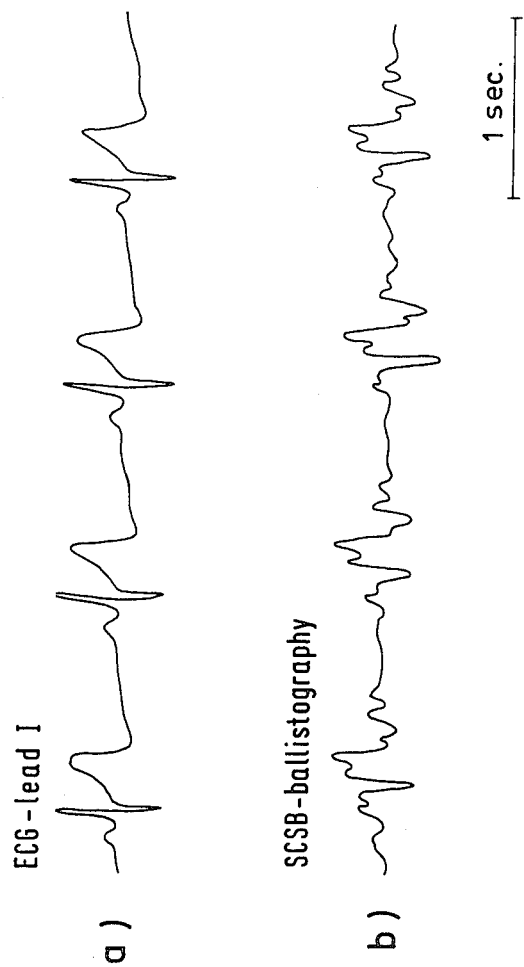
In FIG. 4, the record a shows the recording obtained with the ECG lead I known in prior art and record b, the equivalent recording obtained by means of ballistography according to the invention.

In FIG. 4 has been illustrated a ballistograph (record b) of the invention together with a simultaneous recording (record a) obtained with the ECG lead I of prior art.

Figure 5:
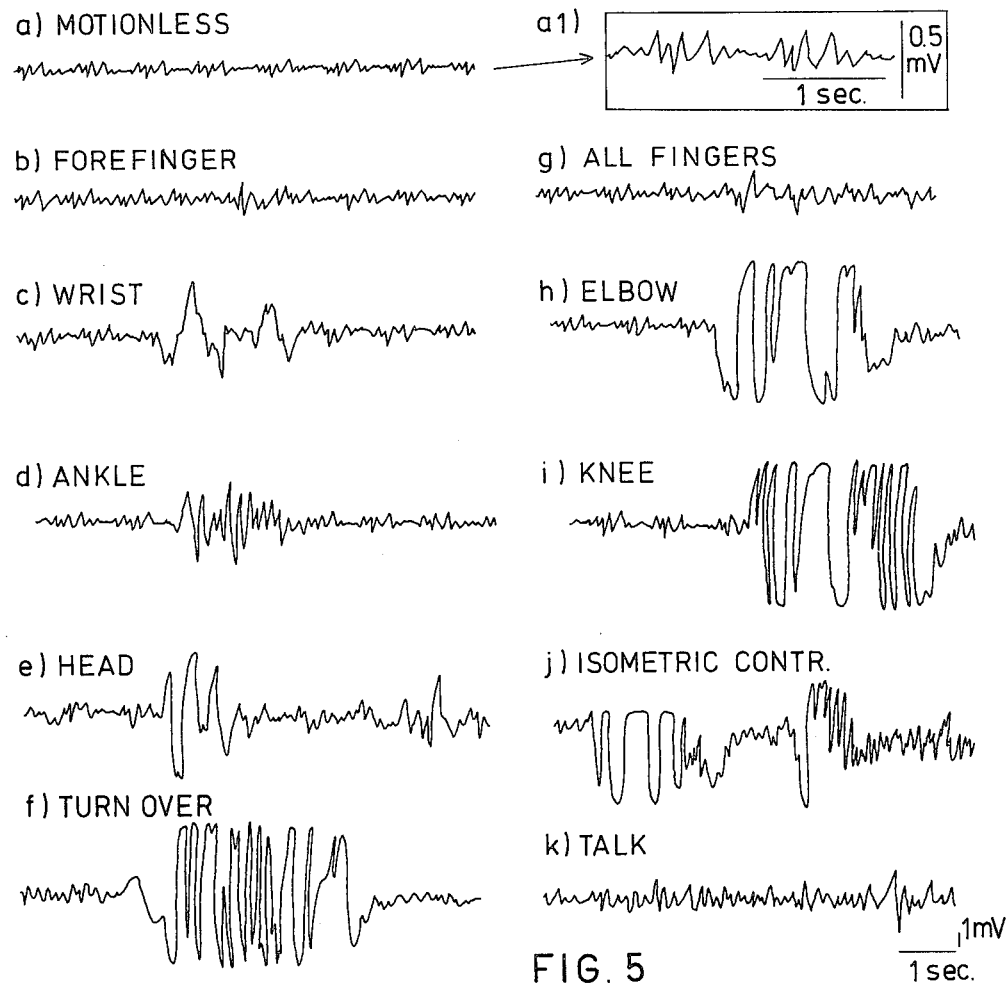
In FIG. 5 have been reproduced the records, recorded by a method according to the invention, produced by eleven different movements.

In FIG. 5 have been reproduced several records produced by various movements of the patient P. The record a represents the completely motionless state, whereby the periodic fluctuations visible in this record reflect the vibrations caused by the patient's heartbeat and breathing. The record a1 duplicates the record a on a larger scale.

The record b represents the record produced by the index finger, c that produced by movement of the wrist, d of the ankle, e of the head, f by the patient turning about, g by movement of all fingers, h by shoulder movement, i by movement of the knee, j by isometric contraction, and k by speech.

In the following, the claims are stated, and various details of the invention may vary within the scope of the inventive idea thereby defined.

We claim:

1. An apparatus for monitoring the movements of a person on a bed or the changes therein, such movements including epileptic convulsive seizures, other deviant movements, tremors, respiration, mechanical cardiac functions, or any other motorics of the person under examination, without attaching a pick-up means directly to the person, said apparatus comprising:
   (a) an active layer;
   (b) an antenna means;
   (c) an amplifying means connected to said antenna means; and
   (d) a monitoring means connected to said amplifying means;

wherein said active layer comprises at least two mutually contacting courses of insulating material having different dielectric constants adapted so that an electrical charge is generated in said layer by relative movement between said contacting courses; and wherein said antenna means is adapted to detect electrical charge generated within said active layer, resulting in an electrical signal being conveyed from said antenna means to the amplifying means and amplified therewith, said amplified signal being conveyed to the monitoring means and converted into a visual, auditory or mechanical signal therewith.

2. An apparatus according to claim 1 wherein the antenna means is adapted to be placed under a mattress and comprises two conductive elements spaced apart from each other.

3. An apparatus according to claim 2 wherein the elements are plates.

4. An apparatus according to claim 2 wherein the elements are nets.

5. An apparatus according to claim 2 wherein the elements are rods.

6. An apparatus according to claim 2 wherein the elements comprise metal films affixed on the opposite surfaces of an insulating layer.

7. Apparatus according to claim 2 characterized in that the active layer and the antenna means are resilient and can be folded or rolled up.

8. Apparatus according to claim 1 wherein the active layer and the antenna means are disposed one upon the other to constitute a recording mattress.

9. Apparatus according to claim 8, characterized in that the recording mattress is located within a protective shield having an inner surface and an outer surface, of which the inner surface consists of an electrically insulating material and the outer surface consists of an electrically conductive material, and said protective shield is connected to a ground terminal of the amplifier means.

10. Apparatus according to claim 9, characterized in that the active layer comprises resilient insulating courses and the antenna means comprises two conductive plates, and said active layer constitutes an insulator between one antenna plate and the protective shield to form a capacitance means.

11. Apparatus according to claim 1, characterized in that one of the courses is a material with airfilled blisters which rest against the other course.

* * * * *